(12) United States Patent
Lizama et al.

(10) Patent No.: US 6,175,981 B1
(45) Date of Patent: Jan. 23, 2001

(54) PORTABLE VIBRATING SLEEP PAD

(76) Inventors: Delilah Navarro Lizama; Reuben Phillip Lizama, both of 861 Hotspring Dr., #C, Phillip, CA (US) 91720

(*) Notice: Under 35 U.S.C. 154(b), the term of this patent shall be extended for 0 days.

(21) Appl. No.: 09/351,425

(22) Filed: Jul. 12, 1999

(51) Int. Cl.[7] .............................. A61H 1/00; A47D 13/06
(52) U.S. Cl. ...................................... 5/655; 5/915; 5/93.1
(58) Field of Search ............................ 5/655, 915, 93.1, 5/658, 663, 503.1, 946, 424, 425, 420

(56) References Cited

U.S. PATENT DOCUMENTS

| | | | |
|---|---|---|---|
| 2,128,978 | * | 9/1938 | Akin ........................ 5/93.1 |
| 2,786,465 | * | 3/1957 | Moxley ..................... 5/915 X |
| 3,321,779 | * | 5/1967 | Kaufman et al. ........... 5/93.1 |
| 3,803,646 | * | 4/1974 | Newerowski ............... 5/931 X |
| 3,877,090 | * | 4/1975 | Schutz ....................... 5/93.1 |
| 4,105,024 | | 8/1978 | Raffel . |
| 4,133,305 | | 1/1979 | Steuer . |
| 4,136,685 | * | 1/1979 | Ramey ....................... 5/915 X |
| 4,326,506 | * | 4/1982 | Kawabata .................. 5/915 X |
| 4,559,929 | | 12/1985 | Hseu . |
| 4,800,600 | * | 1/1989 | Baum ........................ 5/93.1 |
| 4,872,229 | | 10/1989 | Brady . |
| 5,007,410 | * | 4/1991 | DeLaney .................... 5/915 X |
| 5,010,611 | * | 4/1991 | Mallett ...................... 5/93.1 X |
| 5,081,722 | * | 1/1992 | Yu ............................ 5/915 X |
| 5,442,710 | * | 8/1995 | Komatsu .................... 5/915 X |
| 5,600,214 | | 2/1997 | Fromson . |
| 5,606,754 | | 3/1997 | Hand et al. . |
| 5,642,539 | | 7/1997 | Kuo . |
| 5,960,493 | * | 10/1999 | Rhey et al. ................. 5/424 |

* cited by examiner

Primary Examiner—Terry Lee Melius
Assistant Examiner—Robert G. Santos
(74) Attorney, Agent, or Firm—Gene Scott-Patent Law & Venture Group

(57) ABSTRACT

A child's bed mat provides a comfortable sleeping surface which includes vibration devices for soothing a child to sleep. A vertical portion of the mat is strapped in an upright attitude to the vertical rungs of a crib, for instance, and enables the placement of a control box out of reach of the child. The mat is constructed so as to be easily folded for portability.

12 Claims, 3 Drawing Sheets

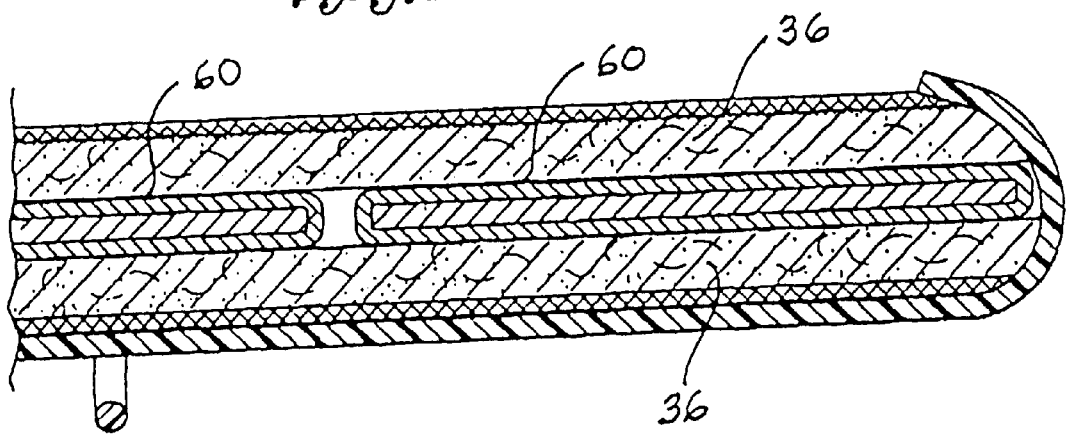
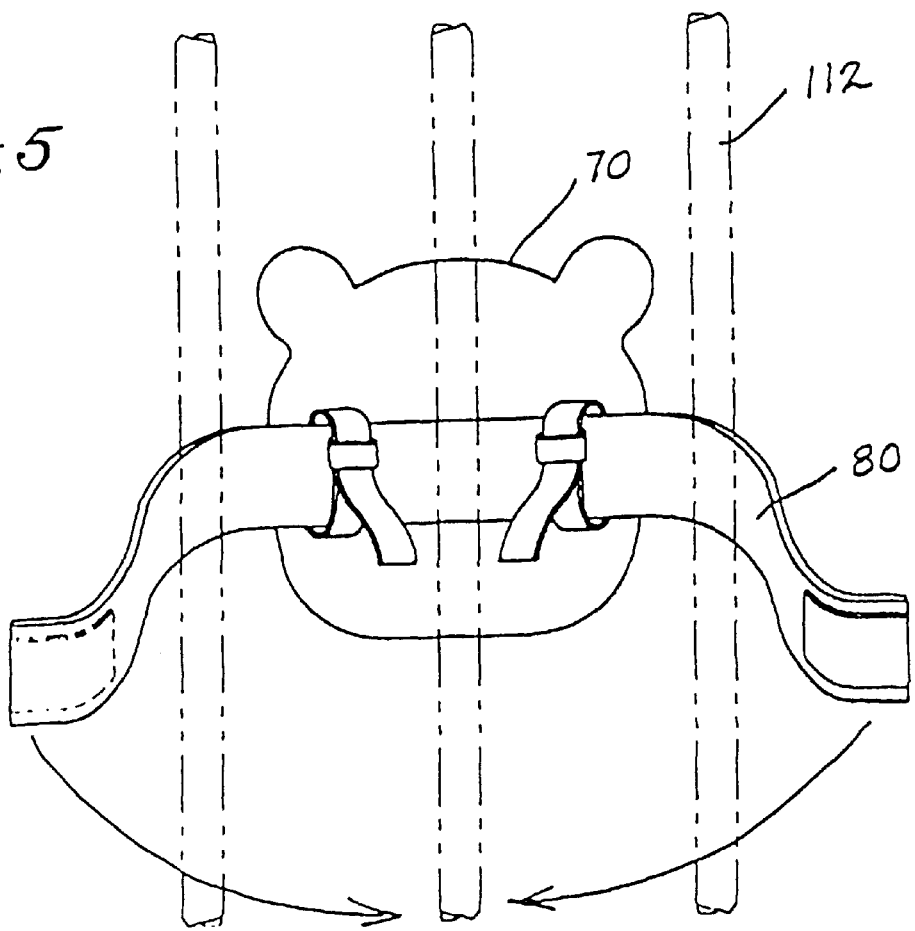

PORTABLE VIBRATING SLEEP PAD

BACKGROUND OF THE INVENTION

1. Field of the Invention

This invention relates generally to a child's mattress or sleeping pad, and more particularly to a novelty sleep pad with vibration capability to lull and sooth a child to sleep.

2. Description of Related Art

The following art defines the present state of this field:

Komatsu, U.S. Pat. No. 5,442,710 describes a body-felt sound unit having a vibration transmitting member imbedded in a human body support member, for example, a chair, a bed, etc., and an electromechanical vibration transducer attached to the vibration transmitting member, the transducer generating mechanical vibration on receipt of a low-frequency current, thereby transmitting the vibration to the human body. The vibration transmitting member of a relatively large area, and the electromechanical vibration transducer is attached to the vibration transmitting member such that the direction of vibration generated from the transducer coincides with the direction of the width of the vibration transmitting member so as to transmit transverse vibration to the vibration transmitting member. Even if the vibration-transmitting member is thin, the apparent rigidity becomes high, so that the transmission of vibration is made effectively.

DeLaney, U.S. Pat. No. 5,007,410 describes a vibrating mattress containing a plurality of independently controlled vibrating units positioned within the mattress in a manner, so as to impart a vibrating resonance along the length of the mattress for the comfort of a person reclining upon the mattress. Each vibrating unit is comprised of a motor and a shaft to which is attached an adjustable eccentric weight that imparts vibrations when in operation. The location of the vibrating units can be changed within the resilient mattress layers, so as to conform to the physical requirements of the individual reclining on the mattress. Battery operated, individual switches with variable resistors control the frequency of each vibrating unit. Operation of the vibrating units may thus impart the desired level of resonance to slowly and quietly lull an individual to sleep.

Kawabata, U.S. Pat. No. 4,326,506 describes a vibratile mat, which comprises a resonating member, vibrating means and a pad. The resonating member includes a plate-like base and a plurality of convex walls arranged and fixed onto the top face of the plate-like base at predetermined intervals. Each convex wall has a number of wart-like small projections formed on the top face thereof. The base and convex wall are composed of a hard plastic material. The vibrating means is placed in a cavity formed by hollowing the resonating member. The pad is disposed on the top face of the resonating member. The pad is composed of a material softer than the material of the resonating member.

Fromson, U.S. Pat. No. 5,60,214 describes an articulated bed having a motor for raising and lowering the bed, a control circuit operated by the user has first user memory for storing a first user variable indicating a user-selected first preferred bed position and a recall button by which the user can command that a handler routine in the control circuit return the bed to the first preferred bed position indicated by the first user variable. Further, the control circuit can have a tracking memory for frequently storing a tracking variable indicating the current position of the bed and a "store" or "program" button or control by which the user can command that the first user variable be set equal to the current tracking variable. Thus, any time the bed is a position preferred by the user, the user can push the store button to store a user variable indicating the preferred bed position in the controller's memory; then afterwards the user can have the bed return to that preferred position by pressing the recall button.

Hseu, U.S. Pat. No. 4,559,929 describes a massage device in the form of a resilient pillow having a cavity therein with at least two spaced vibrator units disposed within the cavity which when activated create a vibratory massaging effect throughout the pillow.

Raffel, U.S. Pat. No. 4,105,024 describes a piece of furniture with nonrotating vibrator motors mounted. Electric power at different frequencies or energy levels is supplied to the respective vibrator motors. Frequency differences in the vibrations result in moving interference waves being produced in the rigid member which waves are imparted to the user of the furniture who experiences a massaging effect. Means are provided for enabling the user of the furniture to control the frequency differential and amplitudes of the driving currents.

Kuo, U.S. Pat. No. 5,642,539 describes a multi-function healthful bed including a bed frame, a bottom bed board, an upper bed board, air valves, a blower, two mufflers, an eccentric motor, four elastic feet supporting four feet of the bed frame, four swayable rods placed on four corner feet of the support plate, a massage bar, an air percolating plate, and a pillow. Air valves fixed in the upper bed board allow air to flow from an air chamber around the body of a user. Warm or cool air may be circulated. The massage bar also includes air valves. The eccentric motor sways the entire bed frame.

Hand, et al. U.S. Pat. No. 5,606,754 describes a vibratory patient support system for providing therapeutic vibrational action or forces to a patient suffering from a respiratory ailment. The vibratory patient support system includes a rigid support frame such as a bed frame with each sac having an upper surface so that the plurality of sacs forms a patient support surface. The inflatable sacs are pressurized and maintained at a predetermined pressure. This predetermined pressure may be a patient height and weight specific pressure profile. A vibrating component is provided separate from the apparatus for pressurizing and maintaining the air sacs at the predetermined pressure. The vibrating component vibrates at least a portion of the patient support surface at a predetermined frequency. In this manner, the plurality of air sacs is maintained at their predetermined frequency. The vibrating mans are further variably controllable so that an operator can vary the frequency, magnitude or amplitude, and duration of the vibrating therapy. The vibratory patient support system may include a specialty low air loss bed configuration including vibrating means for vibrating a portion of a patient support surface of the low air loss sacs at the predetermined frequency.

Yu, U.S. Pat. No. 5,081,722 describes a baby crib comprising two symmetrical side frames and two grilles transversely connected between said two symmetrical side frames at two opposite ends. The bed floor members each have an axle at one end and positioning bolts at the opposite end for positioning bed floor members into circular recesses and positioning holes according to the desired angle of inclination. Sound detectors and humidity sensors are provided to detect discomfort situations and thus trigger alarms and/or comforting devices.

Brady, U.S. Pat. No. 4,872,229 describes a waterproof inflatable massage air mattress having an inflatable head cushion portion that is spaced a predetermined distance from its inflatable body cushion portion. In the space there between is formed a vibrator cushioned portion. The vibrator cushion portion has a chamber closed at its rear end and its front end is opened and closed by a water impermeable linear seal. A vibrator assembly is removably received within the chamber and it is formed from the tubular foam core within which is positioned a vibrator unit. The vibrator unit has a vibrator motor and batteries that are electrically connected together and also connected to a button switch that is mounted in the rear end wall of the tubular foam core. A primary flap and a secondary flap provide protective cover for the water impermeable linear seal.

Steuer, U.S. Pat. No. 4,133,305 describes a relaxation apparatus which includes a mattress consisting essentially of an inflatable hollow body defining an interior space and having an upper reclining surface area for carrying a human body. An air pump is connected to the hollow body for inflating it with air. A vibrating device cooperates with the pump for periodically varying the pressure in the interior space at a preselected frequency so as to raise and lower the reclining surface area periodically. The vibrating device includes a control system for varying the preselected frequency within a range containing the breathing rates.

The prior art teaches mats, mattresses and beds with vibration and sound. Single and multiple vibration units are described and shown. Vibration is combined with posturing furniture and air, water, foam and other types of structures in health related applications. However, the prior art does not teach that a portable mat may be constructed with vibration control and that such may be combined with a child's crib in an apparatus with novelty features. The present invention fulfills these needs and provides further related advantages as described in the following summary.

SUMMARY OF THE INVENTION

The present invention teaches certain benefits in construction and use which give rise to the objectives described below.

The present invention provides a child's bed mat adapted with a comfortable sleeping surface which includes vibration devices for soothing a child to sleep. A vertical portion of the mat is strapped in an upright attitude to the vertical rungs of a crib, for instance, and enables the placement of a control box out of reach of the child. The mat is constructed so as to be easily folded for portability.

A primary objective of the present invention is to provide a sleeping mat having advantages not taught by the prior art.

Another objective is to provide such a mat with vibration control.

A further objective is to provide such a mat constructed for easy folding for portability.

A still further objective is to provide such a mat that resembles a friendly animal.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings:

FIG. 4 is a sectional view thereof taken along line 4—4 in FIG. 1; and

FIG. 5 is a rear elevational view of attachment straps holding a vertically oriented portion thereof.

DETAILED DESCRIPTION OF THE INVENTION

Figure 1:
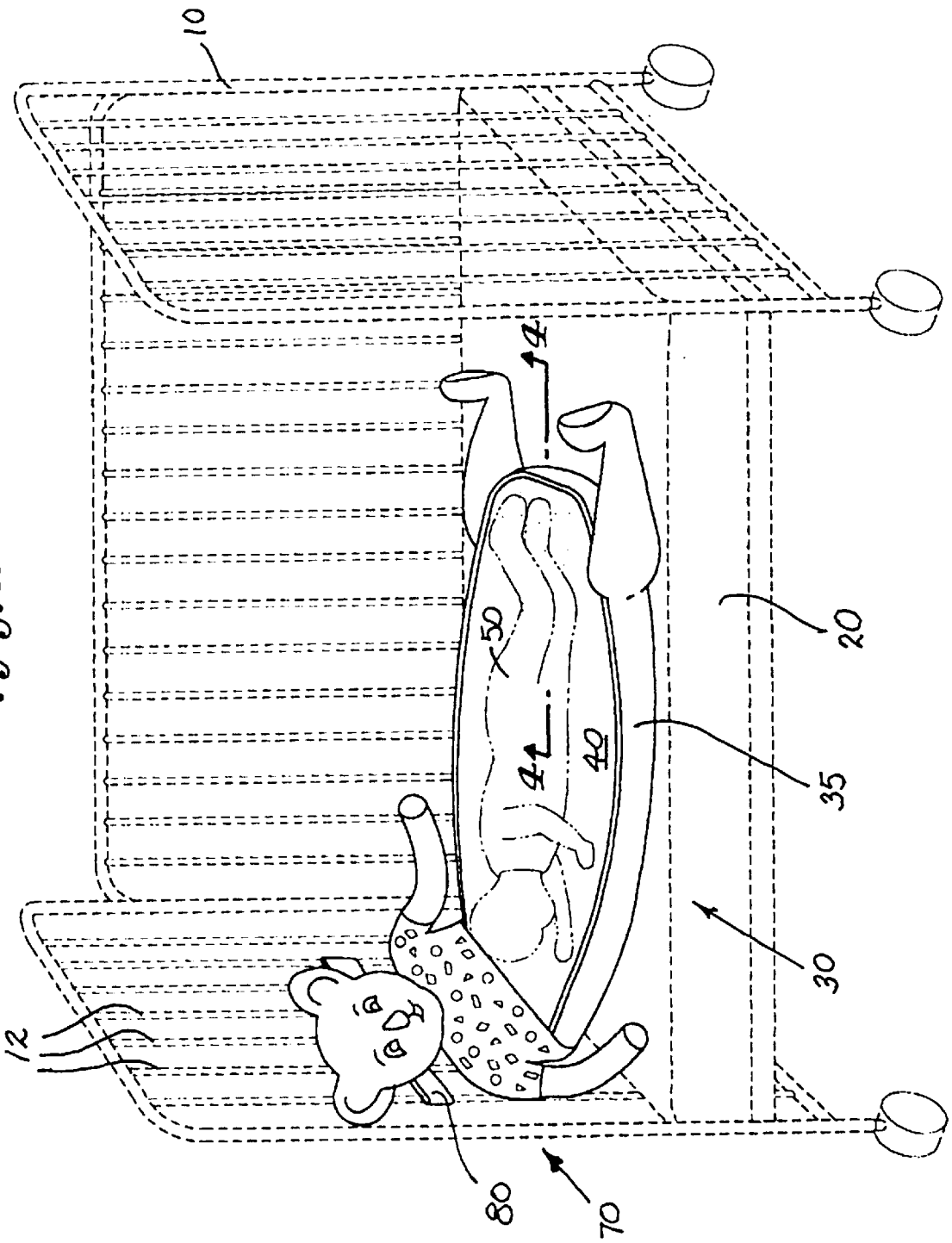
FIG. 1 is a perspective view of the preferred embodiment of the present invention.

The above described drawing figures illustrate the invention, an apparatus comprising, in combination, (see FIG. 1) a crib, bed or other child sleeping apparatus 10 including a support such as a mattress 20, and a crib mat 30 including a horizontal portion 35 providing a horizontal surface 40 for supporting a child 50 in slumber. Engaged within the crib mat 30 (horizontal portion) are a plurality of vibrational enclosures 60 which are flat and relatively stiff walled boxes for supporting vibratory equipment. The crib mat 30 further provides an upwardly extending portion 70 providing, as best seen in FIG. 5, a means for removable engagement 80, such as a strap assembly, for engagement with at least one of the vertical rungs 12 of a crib 10 for restraining the apparatus from moving within the crib 10. The upwardly extending portion 70 encloses a control box 90 for control of a vibration program. An electrical circuit 100 provides, within the control box 90, a means for control of the vibration program and such may be any of a variety of electrical means such as switches, timers and various common circuit elements and stages as are well within the skill of those in the electrical engineering art to conceive and fabricate. The circuit 100 further provides a plurality of electrical vibratory devices 110 such as mechanical vibration elements of any common variety, each of the vibratory devices 110 being enclosed in one of the vibrational enclosures 60. A control panel 120 is enabled for being permanently fixed to the upwardly extending portion 70, or for removable attachment thereto. In the preferred embodiment, the control panel 120 is positioned adjacent to the upwardly extending portion 70 and directed away, and external to the vertical rungs 12 of the crib 10 and interconnected with the apparatus via an electrical interconnection such as a small electrical wire between the control panel 120 and the control box 90 which is within the upwardly extending portion 70, for enabling adjustment of a vibration program in the apparatus. The control panel 120 may also be a hand held remote control device as is well known and its communication with the control box 90, in that embodiment, is via any of the well known wave energy methods such as infrared or radio frequency waves.

Figure 2:
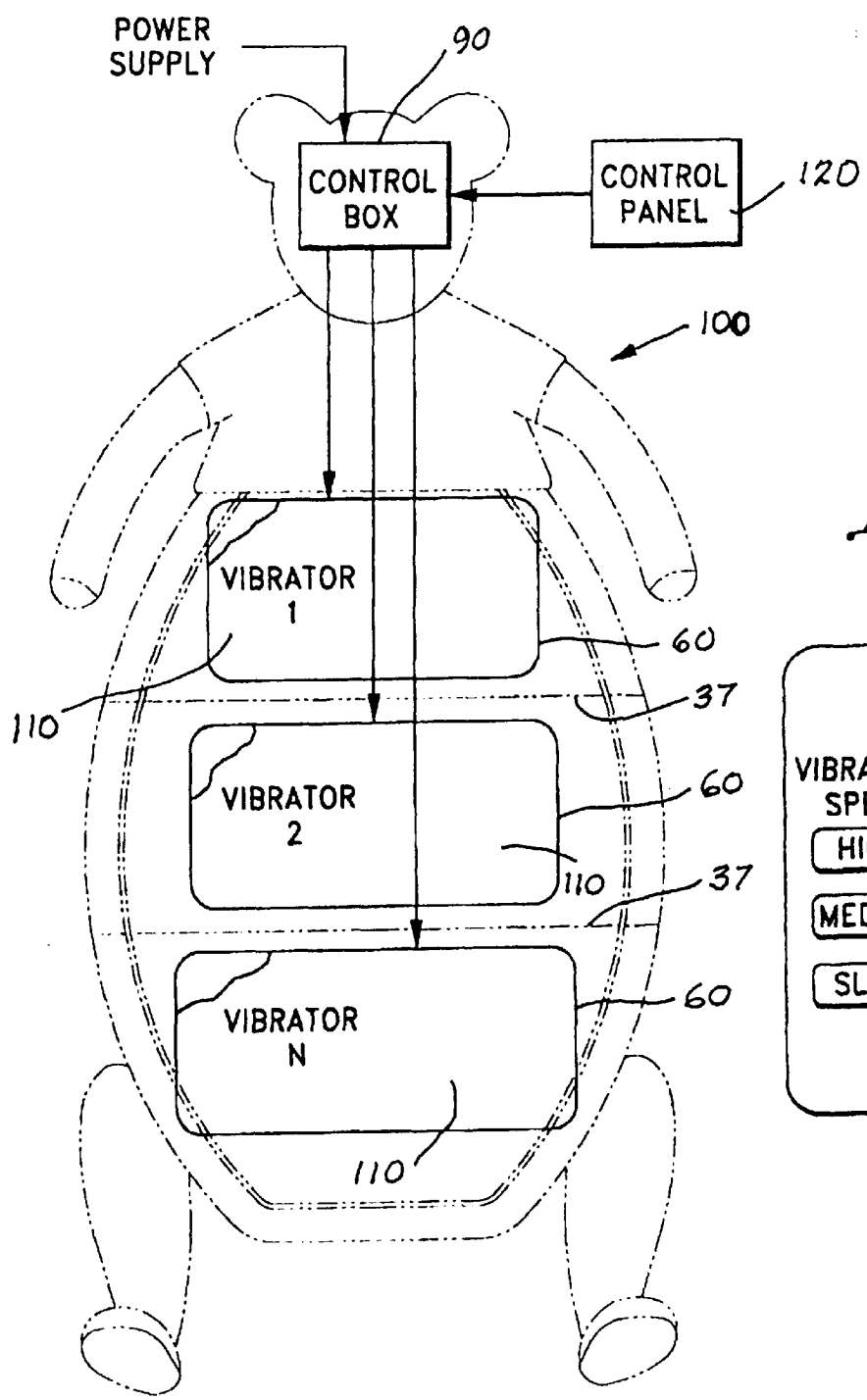
FIG. 2 is a schematic block diagram thereof.
Figure 3:
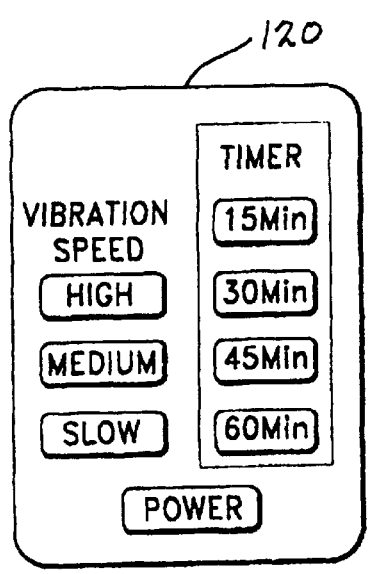
FIG. 3 is a representation of a control panel thereof.

The horizontal portion 35 of the crib mat 30 preferably includes a pair of foam cushioning layers 36, wherein the vibrational enclosures 60 are positioned and sandwiched between said layers. Inventively, the vibrational enclosures 60 are spaced apart, as shown in FIG. 2, in a manner for enabling the crib mat to be folded along lines 37, for placing the vibrational enclosures in a vertical stack (not shown). Inventively, the upwardly extending portion 70 is configured to resemble the upper torso and head of an animal or other recognizable figure or element, and the horizontal portion 35 is configured to resemble a lower torso of the animal or other recognizable figure acceptable and endearing to the child 50. The vibration program control means, i.e., the control panel 120 provides enablement for setting a vibration magnitude and a vibration duration as can be clearly seen in FIG. 3. FIG. 3 shows buttons which may be depressed for setting these two parameters. The circuit enablement for such control is well within the ability of those of skill in the art.

Clearly, the crib 10 and mat 30 may be considered as a combination with separate features providing a synergistic combination as for example wherein the upwardly extending portion of the invention is supported by the crib's rungs 112 so as to be supported in the upright attitude and to hold the mat 35 in a preferred position in the crib 10. Also, the mat apparatus 35 of the present invention clearly defines, by its construction and operation, over the prior art and is therefore presented as an invention by itself.

In use, the present invention apparatus is placed into a crib and fixed in place as shown in FIG. 1 so that it cannot move about the crib and so that the upright portion 70 is positioned for providing an attractive icon easily recognized by the child 50. The child is placed as shown in FIG. 1 onto the horizontal portion 35 and the vibratory program is set, i.e., a vibration magnitude and duration. The vibration provides a soothing and seep inducing means for enabling the child 50 to quickly fall into a deep sleep. After the child is asleep, the vibration times out.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. An apparatus comprising:
    a crib mat including a horizontal portion providing a horizontal surface for supporting a child in slumber, and engaged within the crib mat at least one vibrational enclosure;
    the crib mat further providing an upwardly extending portion providing a means for removable engagement with at least one of the vertical rungs of a crib for restraining the apparatus from moving within the crib, the upwardly extending portion enclosing a control box for control of a vibration program;
    an electrical circuit providing, within the control box, a means for control of the vibration program, and at least one electrical vibratory device, the at least one vibratory device being enclosed in the at least one vibrational enclosure;
    a control panel enabled for attachment to the removable engagement means in a position directed away, and external to the vertical rungs of the crib, the electrical circuit including an electrical interconnection between the control panel and the control box for enabling adjustment of a vibration program in the apparatus.

2. The apparatus of claim 1 wherein the crib mat includes a pair of foam cushioning layers, the at least one vibrational enclosure being positioned and sandwiched between said layers.

3. The apparatus of claim 2 wherein the at least one vibrational enclosure is a plurality of such vibrational enclosures positioned in a manner for enabling the crib mat to be folded for placing the vibrational enclosures in a vertical stack.

4. The apparatus of claim 1 wherein the upwardly extending portion is configured to resemble the upper torso and head of an animal and the horizontal portion is configured to resemble a lower torso of the animal.

5. The apparatus of claim 1 wherein the vibration program control means provides for means for setting a vibration magnitude and a means for setting a vibration duration.

6. A combination crib and sleeping mat apparatus comprising:
    a crib having a plurality of vertical crib runes defining a side enclosure of the crib;
    a crib mat including a horizontal portion providing a horizontal surface for supporting a child in slumber, and engaged within the crib mat at least one vibrational enclosure;
    the crib mat further providing an upwardly extending portion providing a means for removable engagement with at least one of the vertical crib rungs of the crib for restraining the apparatus from moving within the crib, the upwardly extending portion enclosing a control box for control of a vibration program;
    an electrical circuit providing, within the control box, a means for control of the vibration program, and at least one electrical vibratory device enclosed in the at least one vibrational enclosure;
    a control panel enabled for attachment to the removable engagement means in a position directed away, and external to the vertical rungs of the crib, the electrical circuit including an electrical interconnection between the control panel and the control box for enabling adjustment of a vibration program in the apparatus.

7. The apparatus of claim 6 wherein the crib mat includes a pair of foam cushioning layers, the at least one vibrational enclosure being positioned and sandwiched between said layers.

8. The apparatus of claim 7 wherein the at least one vibrational enclosure is a plurality of such enclosures spaced apart in a manner for enabling the crib mat to be folded for placing the vibrational enclosures in a vertical stack.

9. The apparatus of claim 6 wherein the upwardly extending portion is configured to resemble the upper torso and head of an animal and the horizontal portion is configured to resemble a lower torso of the animal.

10. The apparatus of claim 6 wherein the vibration program control means provides for means for setting a vibration magnitude and a means for setting a vibration duration.

11. An apparatus comprising:
    a crib mat providing an upwardly extending portion including a means for removable engagement with at least one of the vertical rungs of a crib for restraining the apparatus from moving within the crib, the upwardly extending portion enclosing a control box for control of a vibration program;
    an electrical circuit providing, within the control box, a means for control of the vibration program, and at least one electrical vibratory device enabled for providing the vibration program within the crib,
    a control panel enabled for attachment to the removable engagement means in a position directed away, and external to the vertical rungs of the crib, the electrical circuit including an electrical interconnection between the control panel and the at least one electrical vibratory device for enabling adjustment of the vibration program.

12. The apparatus of claim 11 wherein the upwardly extending portion is configured to resemble the upper torso and head of an animal.

* * * * *